United States Patent
Mallick et al.

(10) Patent No.: US 7,125,724 B2
(45) Date of Patent: Oct. 24, 2006

(54) METHOD FOR IDENTIFICATION AND/OR DIAGNOSIS OF REM SLEEP LOSS FROM BLOOD SAMPLES

(75) Inventors: Birendra Nath Mallick, New Delhi (IN); Santosh Kumar Kar, New Delhi (IN); Bibhuti Bhusan Mishra, New Delhi (IN); Vibha Madan, New Delhi (IN)

(73) Assignee: Jawaharlal Nehru University, New Delhi (IN)

( * ) Notice: Subject to any disclaimer, the term of this patent is extended or adjusted under 35 U.S.C. 154(b) by 374 days.

(21) Appl. No.: 10/622,128

(22) Filed: Jul. 17, 2003

(65) Prior Publication Data

US 2005/0014277 A1 Jan. 20, 2005

(51) Int. Cl.
*G01N 33/00* (2006.01)

(52) U.S. Cl. ...................................................... 436/86

(58) Field of Classification Search .................. 436/86
See application file for complete search history.

(56) References Cited

FOREIGN PATENT DOCUMENTS

| DE | 28 01 918 | 7/1979 |
|---|---|---|
| JP | 02 166202 | 6/1990 |
| JP | 04 350107 | 12/1992 |
| JP | 2004 124155 | 4/2004 |
| WO | 01/17671 | 3/2001 |
| WO | 03/080275 | 10/2003 |

OTHER PUBLICATIONS

Hall et al. "Glycosylated hemoglobins and glycosylated plasma proteins in the diagnosis of diabetes mellitus and impaired glucose tolerance" Diabetes Care, Mar.-Apr., 7(2): 147-50 (1984) abstract.*

Wait et al. "Proteins of rat serum, urine and cerebrospinal fluid: VI. Further protein identifications and interstrain comparison," Electrophoresis, 22, 3043-3052 (2001).*

McFarland et al. "Clinical value of glycosylated serum protein and glycosylated hemoglobin levels in the diagnosis of gestational diabetes mellitus," Obstetrics & Gynecology, 64:516-518 (1984) abstract.*

Durand et al. "Protein Glycosylation and Diseases: Blood and Urinary Oligosaccharides as Markers for Diagnosis and Therapeutic Monitoring," Clinical Chemistry 46:6 795-805 (2000).*

Mallick et al. "Norephinephrine-Stimulated Increase in Na+, K+-ATPase Activity in the Rat Brain is Mediated Through alpha1A-Adrenoceptor Possibly by Dephosphorylation of the Enzyme," J. Neurochem. 74, 1574-1578 (2000).*

Takahashi et al. "Inhibition of tumor necrosis factor in teh brain suppresses rabit sleep," Pflugers Arch. 431(2): 155-60 (1995) abstract.*

Tobler et al. "Sleep and Sleep Regulation in Normal and Prion Protein Deficient Mice," The Journal of Neuroscience, 17(5): 1869-1879(1997).*

Deboer et al. "Tumor Necrosis Factor (TNF) Ligand and TNF Receptor Deficiency Affects Sleep and the Sleep EEG," J. Neurophysiol., 88: 839-846 (2002).*

Patent Abstracts of Japan of JP 04-350107 dated Dec. 4, 1992.

Patent Abstracts of Japan of JP 02-166202 dated Jun. 26, 1990.

Patent Abstracts of Japan of JP 2004-124155 dated Apr. 22, 2004.

* cited by examiner

*Primary Examiner*—Monique T. Cole
(74) *Attorney, Agent, or Firm*—Ladas & Parry

(57) ABSTRACT

The present invention relates to a method for identification and/or diagnosis of REM sleep loss. More particularly, the present invention relates to a method for identification and/or diagnosis of REM sleep loss from blood samples.

6 Claims, 15 Drawing Sheets

SDS-PAGE SERUM PROTEIN PROFILE OF REMSD RAT

REMSD-RAT1-0D:
Serum sample obtained just before the start of REM sleep deprivation REMSD-RAT1-4D:
Serum sample obtained after 4 days of REM sleep deprivation Two-dimensional SDS PAGE serum proteins profile of one rat on different days, before and after REM sleep deprivation and also after recovery from REM sleep deprivation.

Two-dimensional SDS PAGE serum proteins profile of one rat on different days, before and after REM sleep deprivation and also after recovery from REM sleep deprivation.

REMSD-RAT1-4R:
Serum sample obtained after 4 days of recovery from 7 days of REM sleep deprivation

REMSD-RAT1-7D:
Serum sample obtained after 7 days of REM sleep deprivation

Two-dimensional SDS PAGE serum proteins profile of one rat on different days, before and after it was put on large platform.

LPC-RAT1-4D: Serum sample obtained from LPC rat after 4 days

LPC-RAT1-7D: Serum sample obtained from LPC rat after 7 days

LPC-RAT1-0D: Serum sample obtained from the LPC rat just before the rat was kept on large platform

SDS-PAGE profile of partially purified rat serum protein fraction bound to conA sepharose-4B.

The ~ 200 kDa rat serum protein was partially purified through DEAE ion-exchange column and concentrated in centriplus-100 HR filtration unit. This partially purified material was further fractionated in the matrix bound fraction by incubating with conA sepharose-4B.

One-dimensional SDS-PAGE of the fractions at each step after passing them through each of the three columns used to purify the protein. Fractions of interest from each column were pooled to be run in the next column.

\* Protein of Interest

|  | 10 | 20 | 30 | 40 | 50 | 60 |
|---|---|---|---|---|---|---|
|  | KKDREAQLC | LFSALLAFLP | FASLLNGNSK | YMVLVPSQLY | TETPEKICLH | LYHLNETVTV |
|  | 70 | 80 | 90 | 100 | 110 | 120 |
|  | TASLISQRGT | RKLFDELVVD | KDLFHCVSFT | IPRLPSSEEE | ESLDINIEGA | KHKFSERRVV |
|  | 130 | 140 | 150 | 160 | 170 | 180 |
|  | LVKNKESVVF | VQTDKPMYKP | GQSVKFRVVS | MDKNLHPLNE | LFPLAYIEDP | KMNRIMQWQD |
|  | 190 | 200 | 210 | 220 | 230 | 240 |
|  | VKTENGLKQL | SFSLSAEPIQ | GPYKIVILKQ | SGVKEEHSFT | VMEFVLPRFG | VDVKVPNAIS |
|  | 250 | 260 | 270 | 280 | 290 | 300 |
|  | VYDEIINVTA | CATYTYGKPV | PGHVKISLCH | GNPTFSSETK | SGCKEEDSRL | DNNGCSTQEV |
|  | 310 | 320 | 330 | 340 | 350 | 360 |
|  | NITEFQLKEN | YLKMHQAFHV | NATVTEEGTG | SEFSGSGRIE | VERTRNKFLF | LKADSHFRHG |
|  | 370 | 380 | 390 | 400 | 410 | 420 |
|  | IPFFVKVRLV | DIKGDPIPNE | QVLIKARDAG | YTNATTTDQH | GLAKFSIDTN | GISDYSLNIK |
|  | 430 | 440 | 450 | 460 | 470 | 480 |
|  | VYHKEESSCI | HSSCTAERHA | EAHHTAYAVY | SLSKSYIYLD | TEAGVLPCNQ | IHTVQAHFIL |
|  | 490 | 500 | 510 | 520 | 530 | 540 |
|  | KGQVLGVLQQ | IVFHYLVMAQ | GSILQTGNHT | HQVEPGESQV | QGNFALEIPV | EFSMVPVAKM |
|  | 550 | 560 | 570 | 580 | 590 | 600 |
|  | LIYTILPDGE | VIADSVKFQV | EKCLRNKVHL | SFSPSQSLPA | SQTHMRVTAS | PQSLCGLRAV |
|  | 610 | 620 | 630 | 640 | 650 | 660 |
|  | DQSVLLQKPE | AELSPSLIYD | LPGMQDSNFI | ASSNDPFEDE | DYCLMYQPIA | REKDVYRYVR |
|  | 670 | 680 | 690 | 700 | 710 | 720 |
|  | ETGLMAFTNL | KIKLPTYCNT | DYDMVPLAVP | AVALDSSTDR | GMYESLPVVA | VKSPLPQEPP |
|  | 730 | 740 | 750 | 760 | 770 | 780 |
|  | RKDPPPKDPV | IETIRNYFPE | TWIWDLVTVW | SSGVTELEMT | VPDTITEWKA | GALCLSNDTG |
|  | 790 | 800 | 810 | 820 | 830 | 840 |
|  | LGLSSVASFQ | AFQPFFVELT | MPYSVIRGEA | FTLKATVLNY | LPTSLPMAVL | LEASPDFTAV |
|  | 850 | 860 | 870 | 880 | 890 | 900 |
|  | PVENNQDSYC | LGANGRHTSS | WLVTPKSLGN | VNFSVSAEAR | QSPGPCGSEV | ATVPETGRKD |

↓ SEE FIG. 9B

F I G. 9A

↑ SEE FIG. 9A

```
      910         920         930         940         950         960
       |           |           |           |           |           |
   TVVKVLIVEP  EGIKKEHTFS  SLLCASDAEL  SETLSLLLPP  TVVKDSARAH  FSVMGDILSS
      970         980         990        1000        1010        1020
       |           |           |           |           |           |
   AIKNTQNLIQ  MPYGCGEQNM  VLFAPNIYVL  KYLNETQQLT  EKIKSKALGY  LRAGYQRELN
     1030        1040        1050        1060        1070        1080
       |           |           |           |           |           |
   YKHKDGSYSA  FGDHNGQGQG  NTWLTAFVLK  SFAQARAFIF  IDESHITDAF  TWLSKQQKDS
     1090        1100        1110        1120        1130        1140
       |           |           |           |           |           |
   GCFRSSGSLL  NNAMKGGVDD  EITLSAYITM  ALLESSLPDT  DPVVSKALSC  LESSWENIEQ
     1150        1160        1170        1180        1190        1200
       |           |           |           |           |           |
   GGNGSFVYTK  ALMAYAFALA  GNQEKRNEIL  KSLDKEAIKE  DNSIHWERPQ  KPTKSEGYLY
     1210        1220        1230        1240        1250        1260
       |           |           |           |           |           |
   TPQASSAEVE  MSAYVVLARL  TAQPAPSPED  LALSMGTIKW  LTKQQNSYGG  FSSTQDTVVA
     1270        1280        1290        1300        1310        1320
       |           |           |           |           |           |
   LDALSKYGAA  TFSKSQKTPS  VTVQSSGSFS  QKFQVDKSNR  LLLQQVSLPY  IPGNYTVSVS
     1330        1340        1350        1360        1370        1380
       |           |           |           |           |           |
   GEGCVYAQTT  LRYNVPLEKQ  QPAFALKVQT  VPLTCNNPKG  QNSFQISLEI  SYMGSRPASN
     1390        1400        1410        1420        1430        1440
       |           |           |           |           |           |
   MVIADVKMLS  GFIPLKPTVK  KLERLGHVSR  TEVTTNNVLL  YLDQVTNQTL  SFSFIIQQDI
     1450        1460        1470
       |           |           |
   PVKNLQPAIV  KVYDYYETDE  VAFAEYSSPC   SSDDQNV
```

F I G. 9B

Western blot immunodetection of our protein serum level in rat after treatment of IL-6 in vivo.
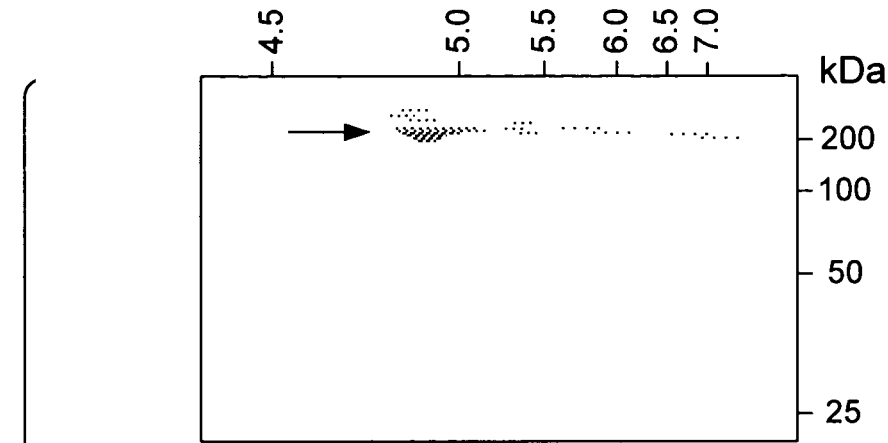
IL6-0D:
Serum sample obtained just before the rat received the first dose of IL-6.
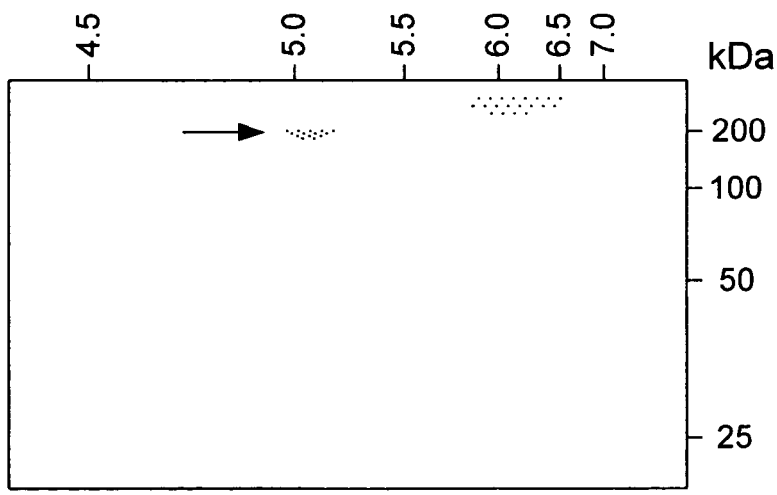
IL6-1D:
Serum sample obtained 1 day after the rat received the first dose of IL-6.
FIG. 12

SEQUENCE LISTING

<160> NUMBER OF SEQ ID NOS: 1

<210> SEQ ID NO 1
<211> LENGTH: 1477
<212> TYPE: PRT
<213> ORGANISM: Rattus norvegicus

<400> SEQUENCE: 1

```
Met Lys Lys Asp Arg Glu Ala Gln Leu Cys Leu Phe Ser Ala Leu Leu
1               5                   10                  15

Ala Phe Leu Pro Phe Ala Ser Leu Leu Asn Gly Asn Ser Lys Tyr Met
            20                  25                  30

Val Leu Val Pro Ser Gln Leu Tyr Thr Glu Thr Pro Glu Lys Ile Cys
        35                  40                  45

Leu His Leu Tyr His Leu Asn Glu Thr Val Thr Val Thr Ala Ser Leu
    50                  55                  60

Ile Ser Gln Arg Gly Thr Arg Lys Leu Phe Asp Glu Leu Val Val Asp
65                  70                  75                  80

Lys Asp Leu Phe His Cys Val Ser Phe Thr Ile Pro Arg Leu Pro Ser
                85                  90                  95

Ser Glu Glu Glu Ser Leu Asp Ile Asn Ile Glu Gly Ala Lys His
            100                 105                 110

Lys Phe Ser Glu Arg Arg Val Val Leu Val Lys Asn Lys Glu Ser Val
        115                 120                 125

Val Phe Val Gln Thr Asp Lys Pro Met Tyr Lys Pro Gly Gln Ser Val
    130                 135                 140

Lys Phe Arg Val Val Ser Met Asp Lys Asn Leu His Pro Leu Asn Glu
145                 150                 155                 160

Leu Phe Pro Leu Ala Tyr Ile Glu Asp Pro Lys Met Asn Arg Ile Met
                165                 170                 175

Gln Trp Gln Asp Val Lys Thr Glu Asn Gly Leu Lys Gln Leu Ser Phe
            180                 185                 190

Ser Leu Ser Ala Glu Pro Ile Gln Gly Pro Tyr Lys Ile Val Ile Leu
        195                 200                 205

Lys Gln Ser Gly Val Lys Glu Glu His Ser Phe Thr Val Met Glu Phe
    210                 215                 220

Val Leu Pro Arg Phe Gly Val Asp Val Lys Val Pro Asn Ala Ile Ser
225                 230                 235                 240

Val Tyr Asp Glu Ile Ile Asn Val Thr Ala Cys Ala Thr Tyr Thr Tyr
                245                 250                 255

Gly Lys Pro Val Pro Gly His Val Lys Ile Ser Leu Cys His Gly Asn
            260                 265                 270

Pro Thr Phe Ser Ser Glu Thr Lys Ser Gly Cys Lys Glu Glu Asp Ser
        275                 280                 285

Arg Leu Asp Asn Asn Gly Cys Ser Thr Gln Glu Val Asn Ile Thr Glu
    290                 295                 300

Phe Gln Leu Lys Glu Asn Tyr Leu Lys Met His Gln Ala Phe His Val
305                 310                 315                 320

Asn Ala Thr Val Thr Glu Glu Gly Thr Gly Ser Glu Phe Ser Gly Ser
                325                 330                 335

Gly Arg Ile Glu Val Glu Arg Thr Arg Asn Lys Phe Leu Phe Leu Lys
            340                 345                 350

Ala Asp Ser His Phe Arg His Gly Ile Pro Phe Phe Val Lys Val Arg
```

-continued

```
                355                 360                 365
Leu Val Asp Ile Lys Gly Asp Pro Ile Pro Asn Glu Gln Val Leu Ile
370                 375                 380
Lys Ala Arg Asp Ala Gly Tyr Thr Asn Ala Thr Thr Asp Gln His
385                 390                 395                 400
Gly Leu Ala Lys Phe Ser Ile Asp Thr Asn Gly Ile Ser Asp Tyr Ser
                405                 410                 415
Leu Asn Ile Lys Val Tyr His Lys Glu Ser Ser Cys Ile His Ser
                420                 425                 430
Ser Cys Thr Ala Glu Arg His Ala Glu Ala His Thr Ala Tyr Ala
            435                 440                 445
Val Tyr Ser Leu Ser Lys Ser Tyr Ile Tyr Leu Asp Thr Glu Ala Gly
    450                 455                 460
Val Leu Pro Cys Asn Gln Ile His Thr Val Gln Ala His Phe Ile Leu
465                 470                 475                 480
Lys Gly Gln Val Leu Gly Val Leu Gln Gln Ile Val Phe His Tyr Leu
                485                 490                 495
Val Met Ala Gln Gly Ser Ile Leu Gln Thr Gly Asn His Thr His Gln
            500                 505                 510
Val Glu Pro Gly Glu Ser Gln Val Gln Gly Asn Phe Ala Leu Glu Ile
            515                 520                 525
Pro Val Glu Phe Ser Met Val Pro Ala Lys Met Leu Ile Tyr Thr
            530                 535                 540
Ile Leu Pro Asp Gly Glu Val Ile Ala Asp Ser Val Lys Phe Gln Val
545                 550                 555                 560
Glu Lys Cys Leu Arg Asn Lys Val His Leu Ser Phe Ser Pro Ser Gln
                565                 570                 575
Ser Leu Pro Ala Ser Gln Thr His Met Arg Val Thr Ala Ser Pro Gln
            580                 585                 590
Ser Leu Cys Gly Leu Arg Ala Val Asp Gln Ser Val Leu Leu Gln Lys
            595                 600                 605
Pro Glu Ala Glu Leu Ser Pro Ser Leu Ile Tyr Asp Leu Pro Gly Met
    610                 615                 620
Gln Asp Ser Asn Phe Ile Ala Ser Ser Asn Asp Pro Phe Glu Asp Glu
625                 630                 635                 640
Asp Tyr Cys Leu Met Tyr Gln Pro Ile Ala Arg Glu Lys Asp Val Tyr
                645                 650                 655
Arg Tyr Val Arg Glu Thr Gly Leu Met Ala Phe Thr Asn Leu Lys Ile
                660                 665                 670
Lys Leu Pro Thr Tyr Cys Asn Thr Asp Tyr Asp Met Val Pro Leu Ala
            675                 680                 685
Val Pro Ala Val Ala Leu Asp Ser Ser Thr Asp Arg Gly Met Tyr Glu
    690                 695                 700
Ser Leu Pro Val Val Ala Val Lys Ser Pro Leu Pro Gln Glu Pro Pro
705                 710                 715                 720
Arg Lys Asp Pro Pro Lys Asp Pro Val Ile Glu Thr Ile Arg Asn
                725                 730                 735
Tyr Phe Pro Glu Thr Trp Ile Trp Asp Leu Val Thr Val Asn Ser Ser
                740                 745                 750
Gly Val Thr Glu Leu Glu Met Thr Val Pro Asp Thr Ile Thr Glu Trp
            755                 760                 765
Lys Ala Gly Ala Leu Cys Leu Ser Asn Asp Thr Gly Leu Gly Leu Ser
770                 775                 780
```

-continued

Ser Val Ala Ser Phe Gln Ala Phe Gln Pro Phe Val Glu Leu Thr
785                 790                 795                 800

Met Pro Tyr Ser Val Ile Arg Gly Glu Ala Phe Thr Leu Lys Ala Thr
                805                 810                 815

Val Leu Asn Tyr Leu Pro Thr Ser Leu Pro Met Ala Val Leu Leu Glu
            820                 825                 830

Ala Ser Pro Asp Phe Thr Ala Val Pro Val Glu Asn Asn Gln Asp Ser
        835                 840                 845

Tyr Cys Leu Gly Ala Asn Gly Arg His Thr Ser Ser Trp Leu Val Thr
    850                 855                 860

Pro Lys Ser Leu Gly Asn Val Asn Phe Ser Val Ser Ala Glu Ala Arg
865                 870                 875                 880

Gln Ser Pro Gly Pro Cys Gly Ser Glu Val Ala Thr Val Pro Glu Thr
                885                 890                 895

Gly Arg Lys Asp Thr Val Val Lys Val Leu Ile Val Glu Pro Glu Gly
            900                 905                 910

Ile Lys Lys Glu His Thr Phe Ser Ser Leu Leu Cys Ala Ser Asp Ala
        915                 920                 925

Glu Leu Ser Glu Thr Leu Ser Leu Leu Pro Pro Thr Val Val Lys
    930                 935                 940

Asp Ser Ala Arg Ala His Phe Ser Val Met Gly Asp Ile Leu Ser Ser
945                 950                 955                 960

Ala Ile Lys Asn Thr Gln Asn Leu Ile Gln Met Pro Tyr Gly Cys Gly
                965                 970                 975

Glu Gln Asn Met Val Leu Phe Ala Pro Asn Ile Tyr Val Leu Lys Tyr
            980                 985                 990

Leu Asn Glu Thr Gln Gln Leu Thr Glu Lys Ile Lys Ser Lys Ala Leu
        995                 1000                1005

Gly Tyr Leu Arg Ala Gly Tyr Gln Arg Glu Leu Asn Tyr Lys His
    1010                1015                1020

Lys Asp Gly Ser Tyr Ser Ala Phe Gly Asp His Asn Gly Gln Gly
    1025                1030                1035

Gln Gly Asn Thr Trp Leu Thr Ala Phe Val Leu Lys Ser Phe Ala
    1040                1045                1050

Gln Ala Arg Ala Phe Ile Phe Ile Asp Glu Ser His Ile Thr Asp
    1055                1060                1065

Ala Phe Thr Trp Leu Ser Lys Gln Gln Lys Asp Ser Gly Cys Phe
    1070                1075                1080

Arg Ser Ser Gly Ser Leu Leu Asn Asn Ala Met Lys Gly Gly Val
    1085                1090                1095

Asp Asp Glu Ile Thr Leu Ser Ala Tyr Ile Thr Met Ala Leu Leu
    1100                1105                1110

Glu Ser Ser Leu Pro Asp Thr Asp Pro Val Ser Lys Ala Leu
    1115                1120                1125

Ser Cys Leu Glu Ser Ser Trp Glu Asn Ile Glu Gln Gly Gly Asn
    1130                1135                1140

Gly Ser Phe Val Tyr Thr Lys Ala Leu Met Ala Tyr Ala Phe Ala
    1145                1150                1155

Leu Ala Gly Asn Gln Glu Lys Arg Asn Glu Ile Leu Lys Ser Leu
    1160                1165                1170

Asp Lys Glu Ala Ile Lys Glu Asp Asn Ser Ile His Trp Glu Arg
    1175                1180                1185

-continued

```
Pro Gln Lys Pro Thr Lys Ser Glu Gly Tyr Leu Tyr Thr Pro Gln
    1190            1195            1200

Ala Ser Ser Ala Glu Val Glu Met Ser Ala Tyr Val Val Leu Ala
    1205            1210            1215

Arg Leu Thr Ala Gln Pro Ala Pro Ser Pro Glu Asp Leu Ala Leu
    1220            1225            1230

Ser Met Gly Thr Ile Lys Trp Leu Thr Lys Gln Gln Asn Ser Tyr
    1235            1240            1245

Gly Gly Phe Ser Ser Thr Gln Asp Thr Val Val Ala Leu Asp Ala
    1250            1255            1260

Leu Ser Lys Tyr Gly Ala Ala Thr Phe Ser Lys Ser Gln Lys Thr
    1265            1270            1275

Pro Ser Val Thr Val Gln Ser Ser Gly Ser Phe Ser Gln Lys Phe
    1280            1285            1290

Gln Val Asp Lys Ser Asn Arg Leu Leu Leu Gln Gln Val Ser Leu
    1295            1300            1305

Pro Tyr Ile Pro Gly Asn Tyr Thr Val Ser Val Ser Gly Glu Gly
    1310            1315            1320

Cys Val Tyr Ala Gln Thr Thr Leu Arg Tyr Asn Val Pro Leu Glu
    1325            1330            1335

Lys Gln Gln Pro Ala Phe Ala Leu Lys Val Gln Thr Val Pro Leu
    1340            1345            1350

Thr Cys Asn Asn Pro Lys Gly Gln Asn Ser Phe Gln Ile Ser Leu
    1355            1360            1365

Glu Ile Ser Tyr Met Gly Ser Arg Pro Ala Ser Asn Met Val Ile
    1370            1375            1380

Ala Asp Val Lys Met Leu Ser Gly Phe Ile Pro Leu Lys Pro Thr
    1385            1390            1395

Val Lys Lys Leu Glu Arg Leu Gly His Val Ser Arg Thr Glu Val
    1400            1405            1410

Thr Thr Asn Asn Val Leu Leu Tyr Leu Asp Gln Val Thr Asn Gln
    1415            1420            1425

Thr Leu Ser Phe Ser Phe Ile Ile Gln Gln Asp Ile Pro Val Lys
    1430            1435            1440

Asn Leu Gln Pro Ala Ile Val Lys Val Tyr Asp Tyr Tyr Glu Thr
    1445            1450            1455

Asp Glu Val Ala Phe Ala Glu Tyr Ser Ser Pro Cys Ser Ser Asp
    1460            1465            1470

Asp Gln Asn Val
    1475
```

METHOD FOR IDENTIFICATION AND/OR DIAGNOSIS OF REM SLEEP LOSS FROM BLOOD SAMPLES

FIELD OF INVENTION

The present invention relates to a method for identification and/or diagnosis of REM sleep loss. More particularly, the present invention relates to a method for identification and/or diagnosis of REM sleep loss from blood samples. The present invention offers a simple yet an effective method for accurately evaluating and diagnosing the REM sleep loss in mammals.

BACKGROUND OF THE INVENTION

Sleep and wakefulness are natural behavioural phenomena present across the species and across age. During sleep, the living being takes rest, recuperates from lost energy and feels afresh. Lack of sleep or lack of adequate sleep due to any reason, for instance, any disease, results in mental as well as physical fatigue.

Sleep has been classified into slow sleep, deep sleep and rapid eye movement (REM) sleep. During slow sleep, the electroencephalogram (EEG), follows synchronized pattern while during REM sleep, the EEG is desynchronized. The REM sleep is unique in the sense that some of the signs during this phase are similar to those during wakefulness while others are similar to those during sleep. Irregular heart beat rate and respiration, periods of involuntary muscle jerks and movements and higher threshold for arousal further characterize the REM sleep. Periods of desynchronized sleep occupy about 20% of the sleeping time and dreams usually occur during this phase of sleep.

Sleep including REM sleep, can be assessed subjectively and behaviourally. However, in order to avoid subjectivity and for adequate quantification, continuous electrophysiological recordings of electroencephalogram (EEG), electrooculogram (EOG) and electromyogram (EMG) are done. One of the disadvantages of this approach is the need for fixing electrodes on the skull for recording EEG, in the muscles of the neck and eye for recording EMG and EOG, respectively. While it may be argued that these procedures are non-invasive, for recording in the humans, they suffer from a major disadvantage of requiring the subject to spend the night in the sleep lab. Even if the subject does not wish to spend the night in a sleep lab, an electrophysiological recording unit has to be moved to the bedside of the patient. Another major disadvantage is that the recording has to be carried out over the night and requires the presence of a trained nurse throughout. A huge quantity of paper recording—of the order of one third of a mile long—must be scored and evaluated by trained personnel. To avoid such drawbacks, prior art has attempted to conduct analysis with the help of computers with relevant software. Nevertheless, the overall elctrophysiological process of recording is quite cumbersome, time consuming and expensive and not readily adaptable to ambulatory or home based monitoring.

Behaviourally, REM sleep loss is reported to cause increased irritability, excitability, sexuality, loss of concentration and coordination, reduced memory consolidation and brain maturity etc. A significant number of early morning road and industry related accidents are attributed to sleep loss including REM sleep loss. Such loss may even lead to social misbehaviour including in work place leading to reduced efficiency and productivity. It has been reported that at any given time, about one third of the adult population is likely to complain of insomnia, while a small proportion complain of being excessively sleepy. The number of patients with sleep related problems have increased dramatically over the years and continues to increase.

Although polysomnography has an important role to play in this regard, its availability and application are very limited. Even a large sleep disorders center can only cater to the need of a relatively small number of patients as compared to the number of patients who are required to be tested. Also, polysomnography does not address all relevant aspects of a disorder. Hence, there is an urgent need to develop a simpler and quicker testing method to evaluate REM sleep loss/disturbance.

OBJECTS OF THE INVENTION

Accordingly, it is an object of the invention to provide a method for diagnosis and/or identification of REM sleep loss in the out patient department (OPD), which does not require hospitalization or admission of the subject/patient to a sleep laboratory.

It is another object of the present invention to provide a method for diagnosis and/or identification of REM sleep loss, which dispenses with the use of complicated machinery such as electroencephalogram (EEG), electrooculogram (EOG) and electromyogram (EMG).

It is yet another object of the present invention to provide a method for diagnosis and/or identification of REM sleep loss, which minimizes chances of human error involved in reading extremely long recordings on paper.

It is another object of the present invention to provide a method for diagnosis and/or identification of REM sleep loss, which is simple to perform and universal in its application.

It is still another object of the present invention to provide a method for diagnosis and/or identification of REM sleep loss, which is cost effective and speedy.

Yet another object of the present invention is to provide an easy means to test levels of REM sleep in subjects/patients and compare with normal values and decide accordingly.

Another object of this invention is to provide an easy handle to the physician to obtain prognosis of a patient even in non-specialized hospitals/health care units (e.g. blood sugar test).

It is yet another object of this invention provide an easy and cost-effective method for testing efficacy and potency of some new chemical/drug on REM sleep.

Its another object of the present invention to provide a simple method to identify quantity of REM sleep deprivation in animals.

It is another object of the present invention to provide an easy and simple method to evaluate the qualitative and quantitative loss of REM sleep at the bedside and may be at home on routine basis.

SUMMARY OF THE INVENTION

The above and other objects of the present invention are achieved by the method of the present invention, which enable accurate and speedy diagnosis of REM sleep loss from the subject's blood sample. Similarly it may be used as a reference for REM sleep deprivation of animals before studying the effects of its deprivation. It may have prognostic value. The present invention is based on the important and novel finding that REM sleep deprivation induces changes in serum protein profile.

According to the invention, blood samples are collected from the patient under usual sterile conditions. If necessary, blood samples may be collected on the $0^{th}$ day and on the 4th and $7^{th}$ day.

Thereafter, serum is collected from the blood samples. Standard method is followed to collect serum from the collected blood. The collected blood is allowed to clot. After that it is left overnight to allow the clot to shrink. It is centrifuged and then the supernatant is collected as serum. The collected serum is stored at conventional conditions until analyzed. Serum samples were separated by conventional methods. Preferred methods are One-dimensional and Two-dimensional electrophoresis. It is noticed that a 200 kDa protein band decreased significantly after REM sleep deprivation.

The present invention thus, provides an effective tool for diagnosing REM sleep loss. The present invention also provides a molecular marker for diagnosing REM sleep loss.

DETAILED DESCRIPTION

The present invention will now be described in greater detail with reference to the following Example where tests were conducted on Rats, which as a person skilled in the art will appreciate is an excellent animal model for human in the area of technology covered by this invention. The present invention will also be described with reference to the accompanying drawings wherein:

FIG. 1 illustrates one-dimensional SDS-PAGE GEL of serum protein profile of one rat before REM sleep deprivation, after 4th, 7th and 9th day REM sleep deprivation and after recovery (REC).

FIG. 2 shows the SDS GEL of serum protein profile of one rat after 4 and 7 days REM sleep deprivation and of another rat after 4 and 7 days on large platform control (LPC).

FIG. 9 shows the sequence of the isolated protein identified as Seq ID # 1.

FIG. 12 shows the same as FIG. 11 except that the rats were injected with interleukin 6 (IL6).

EXAMPLE

Figure 1:
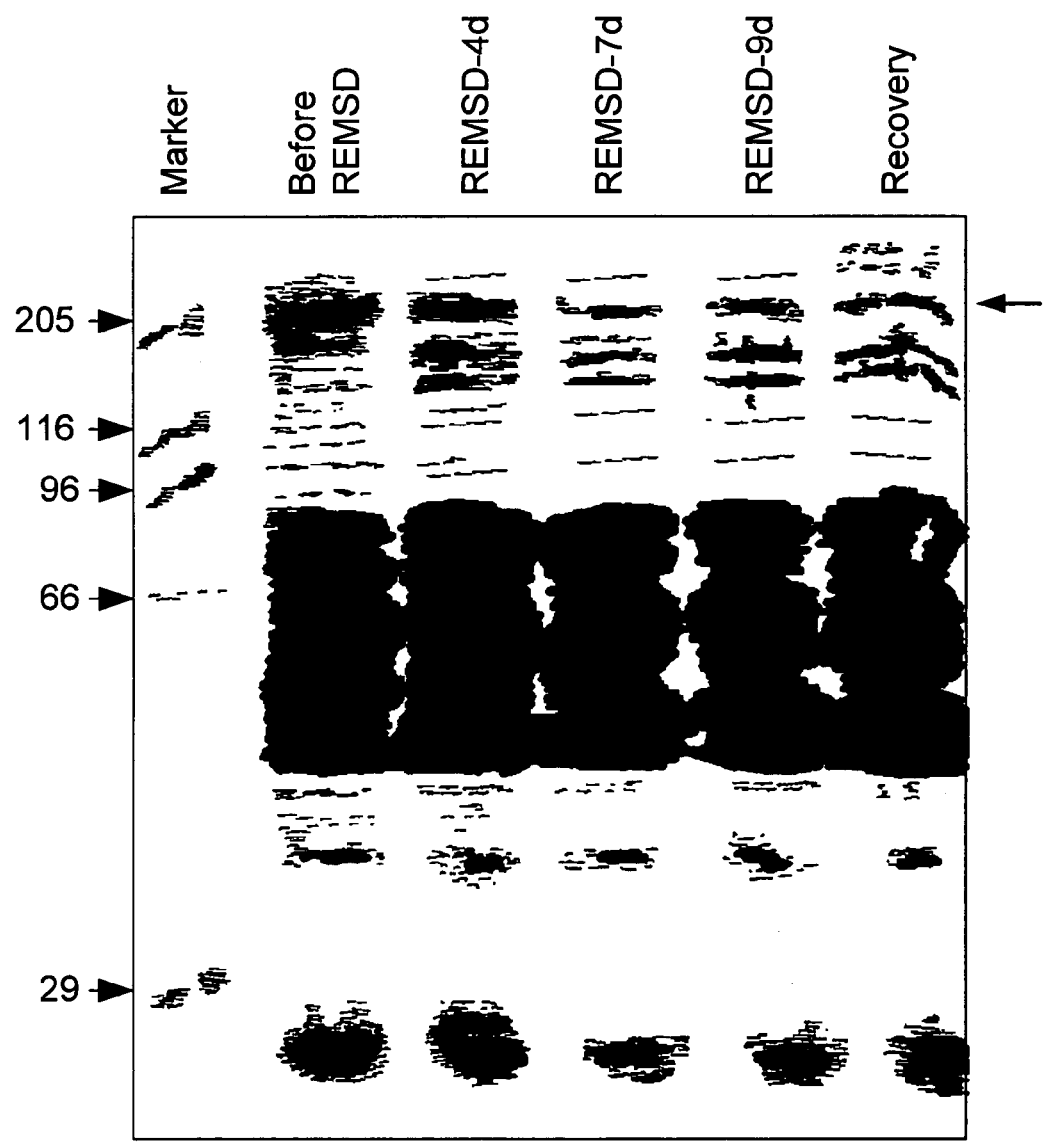

In the present experiment, rats were used as animal models. However, as a skilled person in the art will appreciate, the same results can be expected in higher mammals including humans.

Experiments were conducted as follows:

REM Sleep Deprivation:

Experiments were conducted on male albino Wistar rats weighing between 225–300 gms. Experimentally REM sleep deprivation was carried out by the classical flower-pot technique that has been most widely used globally. The method has successfully been used in this laboratory for more than a decade and a good number of research papers have been published from this laboratory using this technique. The experimental (E) rats were maintained on small platform (SP) having a diameter of 6.5 cm projecting above a pool of water. The rats on the SP could sit and stand and also had easy access to food and water ad libitum, however, they were unable to assume the relaxed posture required for REM sleep. The REM sleep deprivation was continued for 4 and 7 days. For control experiments rats were maintained for equivalent period in identical environmental conditions on larger platforms of 13 cm diameter placed over a pool of water—the large platform control (LPC). In other sets of experiments the E rats, after the end of REM sleep deprivation, were allowed to recover from the effect of REM sleep deprivation by allowing them to have normal sleep for 4 and 7 days—the recovery group (Rec). For recovery the rats were allowed to stay in normal rat cages.

REM Sleep Deprivation Induced Changes in Serum Protein Profile:

Blood samples were collected from rats on the 0th day i.e. at the start of REM sleep deprivation or before placing the control rats on large platform. Also blood samples were collected on the 4th and 7th day after REM sleep deprivation or after the rats spent equivalent period on the large platform (Control). Blood samples were also collected after the rats were REM sleep deprived and then allowed to sleep normally for 4 and 7 days i.e. after recovery of lost REM sleep. In another control experiment blood sample was collected and then the rats were allowed to continuously swim for 6 hours. Blood sample was collected at the end of the 6 hrs swimming. This was done to study if the change in the blood protein was due to excessive muscle movement as one might argue could be due to prolonged stay on the small platform during REM sleep deprivation.

Serum, Collection:

Standard method was followed to collect serum from the collected blood. The collected blood was allowed to clot 2 hours at room temperature. After that it was left at 4° C. overnight to allow the clot to shrink. It was centrifuged at 10,000 rpm for 10 mins. at 4° C. and then the supernatant was collected as serum. The collected serum was stored at −80° C. till analysed.

Study of Serum Protein Pattern by One and Two Dimensional Electrophoresis:

Serum samples were separated by One-dimensional 7.5–15% gradient polyacrylamide gel electrophoresis (SDS-PAGE) and stained with coommassie BR-250. For Two-dimensional electrophoresis, the pH gradient was established using 1.6% Bio-Lyte pH 5–8 and 0.4% of Bio-Lyte pH 3–10. The serum samples were then isoelectrically focussed (IEF) when they were separated according to their pI. In the second dimension these IEF gels were run in 10% SDS PAGE. A 200 kDa protein band decreased significantly after REM sleep deprivation.

SDS PAGE Analysis of Serum Samples:

SDS-PAGE was performed following standard method using discontinuous buffer gradient.

Chemicals Used:

| 2 X Sample Buffer | 100 ml |
|---|---|
| Tris base | 1.52 gm |
| Glycerol | 20.0 ml |
| SDS | 2.0 gm |
| β-Mercaptoethanol | 2.0 ml (for reducing condition) |
| Bromophenol blue | 0.002% |
| Electrophoresis buffer | 1 Liter |
| Tris base | 3.02 gm |
| Glycine | 14.4 gm |
| SDS | 1.0 gm |
| pH is auto adjusted to 8.3 | |

Samples: Serum Samples from REM Sleep Deprived and Control Rats.

| Composition of SDS separating gel and Resolving gel Solution for 10% Acrylamide gel (20 ml) - Separating gel 30% Acrylamide mix 6.7 ml (29.2% Acrylamide & 0.8% Bis-acrylamide) | |
|---|---|
| 1.5 M Tris-CI, pH 8.8 | 5.0 ml |
| 10% SDS | 0.2 ml |
| 10% APS | 0.2 ml |
| TEMED | 0.01 ml |
| Distilled water | 7.9 ml |
| Stacking Gel - 5 ml | |
| 30% Acrylamide mix | 0.83 ml |
| 1.0 M Tris-CI, pH 6.8 | 0.63 ml |
| 10% SDS | 0.05 ml |
| 10% APS | 0.05 ml |
| TEMED | 0.005 ml |
| Distilled water | 3.4 ml |

Method:

SDS (sodium dodecyl sulphate) gel was prepared following standard method. The stacking gel solution was layered on top of the resolving gel and the plastic comb was inserted into it to make wells for sample loading. The stacking gel was left for polymerization. Samples were prepared by taking 2.5 ul of serum, 18 ul of DD $H_2O$ and 20 ul of 2×-sample buffer and boiled for 5 minutes, to denature and reduce the disulfide bonds of the proteins.

Samples were briefly spun in a tabletop centrifuge to settle down any precipitated proteins and then loaded into the wells of the stacking gel.

Initially an electric field of constant 80 volts was applied across the electrodes till the proteins were stacked to a plane before crossing the stacking gel. The voltage was increased to 100 volts (constant) and electrophoresis was continued till the bromophenol dye front reached the bottom of the resolving gel and then gel was processed for staining of the proteins.

Staining the Polyacrylamide Gels for Visualization of Protein Bands:

Fixing solution: Methanol 25% and acetic acid 5% in deionized water.

Staining solution: Coommassie brilliant blue (CBB), 0.05% in 50% methanol and 5% Acetic acid.

CBB was dissolved in a small amount of methanol, then more methanol added followed by acetic acid and finally volume was adjusted with deionized water.

Destaining solution: 5% methanol, 7.5% acetic acid in double distilled water

Method:

The gel, after electrophoresis, was incubated in 10 volumes of fixing solution for 20 min on a shaker. The gel was stained by shaking in five volumes of CBB solution for 4 h to overnight. Staining solution was removed and the gel was rinsed with deionized water. The gel was destained in 20 volumes of destaining solution for 2–3 hours with several changes until the background was clear.

Characterization of the 200 kDa Protein:

Quantification of the Relative Percentage Change of the 200 kDa Protein with REM Sleep Deprivation:

The densitometric analysis of protein bands was done using Scion Image analyzer programme. The intensity of the 200 kDa band and transferrin band in each sample was calculated. To rule out any nonspecific error the transferrin band was taken as an internal control. The relative concentration of the 200 kDa band with respect to transferrin was estimated from REM sleep deprived, free moving control, large platform control and recovered from REM sleep deprivation sample gels.

Purification of the 200 kDa Protein:

The protein was purified and used for antibody development using standard method.

Immunoblot (Western Blot) Analysis of the Serum Samples from REM Sleep Deprived Rats:

Rat serum samples were run in 10% SDS PAGE and the proteins were transferred (blotted) onto nitrocellulose paper. Immunodetection was done using rabbit polyclonal antisera against the above mentioned 200 KDa rat serum protein.

As can be seen from FIG. 1, this figure illustrates one-dimensional SDS-PAGE GEL of serum protein profile of one rat before REM sleep deprivation, after 4th, 7th and 9th day REM sleep deprivation and after recovery (REC). Marker lane indicates the positions of proteins of known molecular weight (as labeled). In each rat, visual comparison of individual protein level revealed that in all the rats the level of a ~200 kDa protein band was lower in REM sleep deprived sample than before the start of deprivation. Further, the protein levels tended to return to normal levels after recovery of REM sleep.

Figure 2:
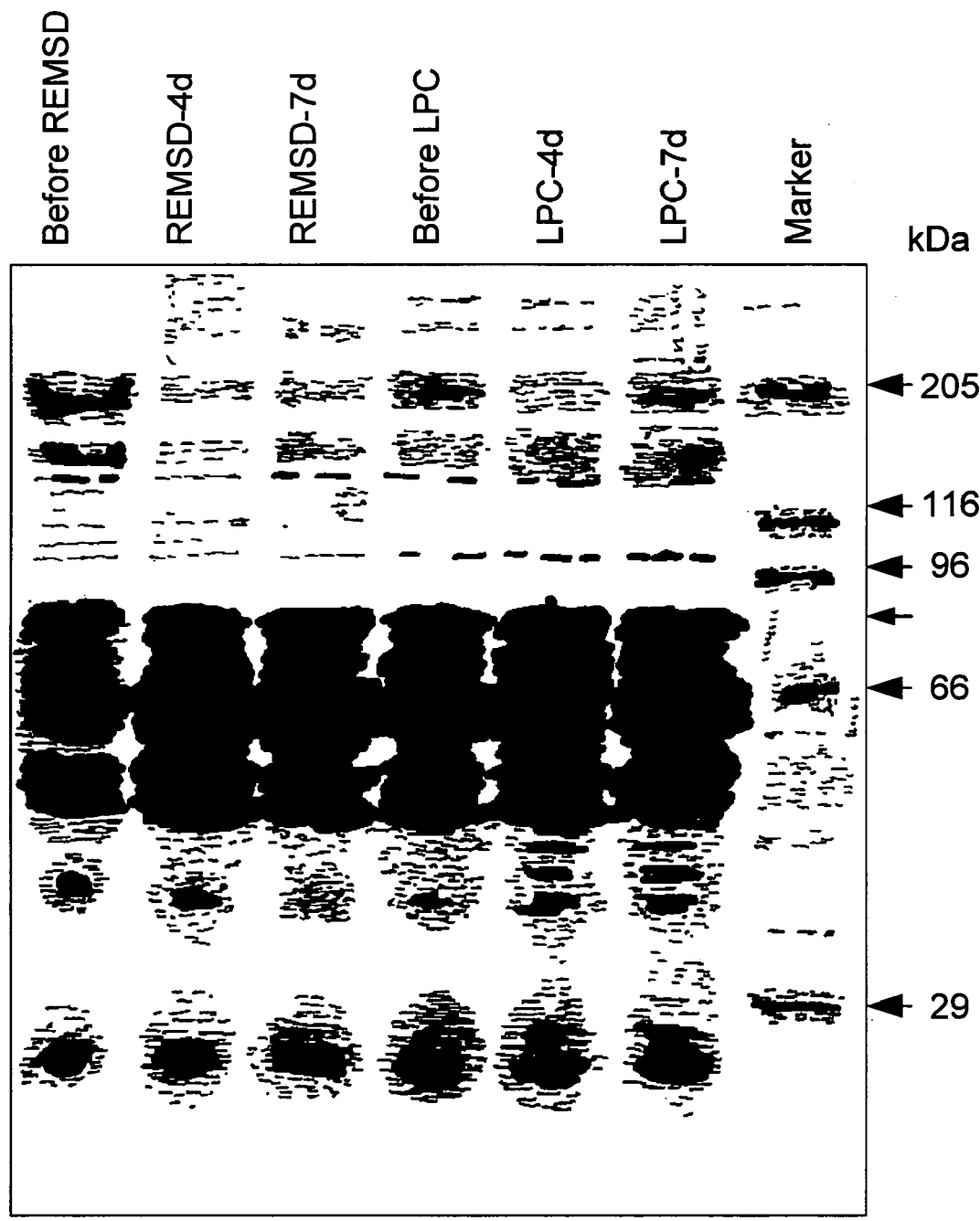

FIG. 2 shows the SDS GEL of serum protein profile of one rat after 4 and 7 days REM sleep deprivation and of another rat after 4 and 7 days in large platform control (LPC). The –marker shows the position of known molecular weight proteins. It may be seen from the figure that the ~200 KDa protein concentration decreased after REM sleep deprivation but it did not change in control rats i.e. if a rat was maintained on large platform.

Figure 3:
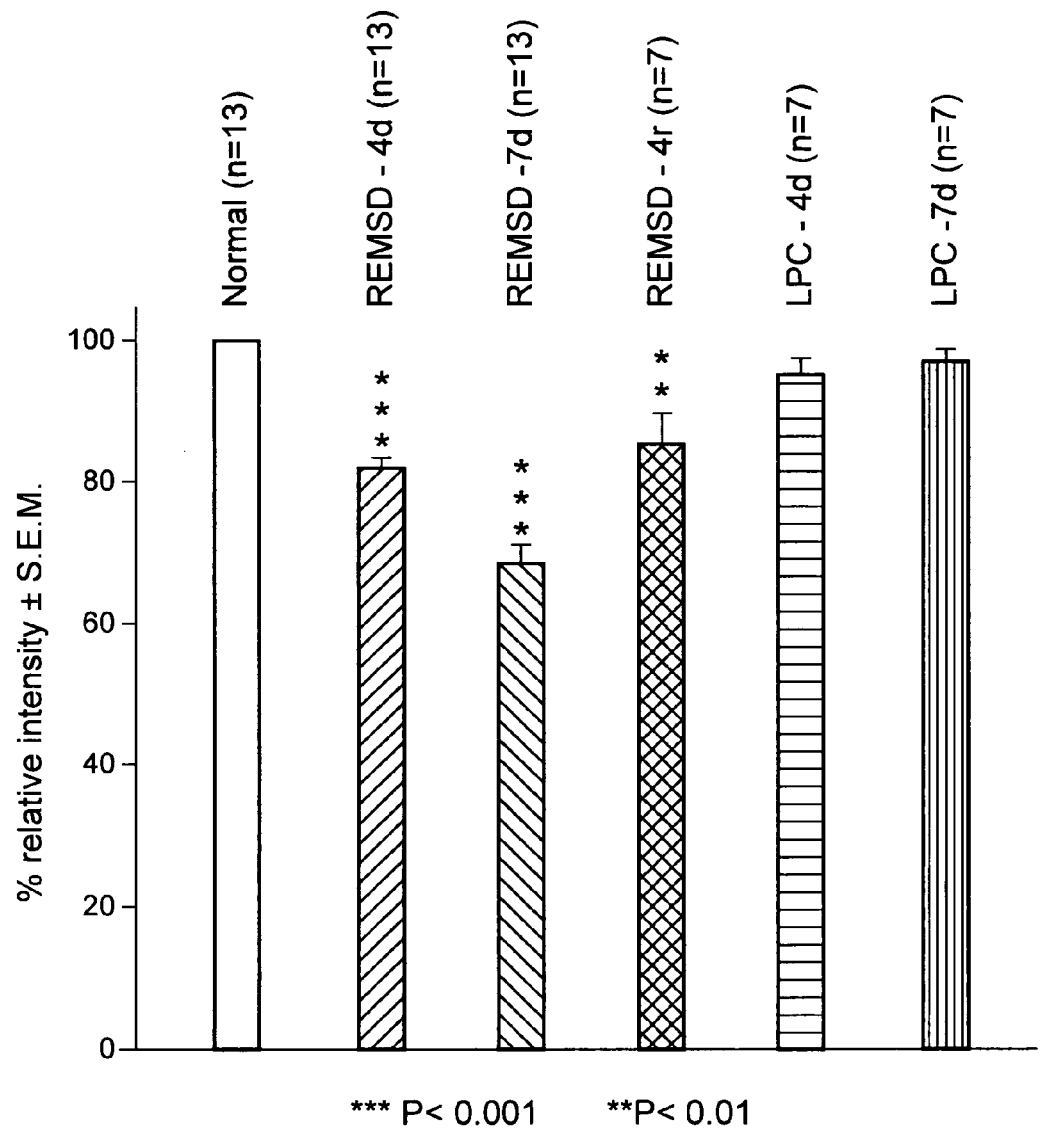
FIG. 3 shows the mean color intensity of the ~200 KDa protein band in the SDS-GEL from 9 rats before and after REM sleep deprivation and after recovery of REM sleep deprivation.

In FIG. 3 the mean color intensity of the ~200 KDa protein band in the SDS-GEL from 9 rats before and after REM sleep deprivation, after recovery of REM sleep deprivation and after maintaining another 9 rats on large platforms were estimated densitometrically. The band intensity of the ~200 KDa band was normalized against an internal control protein (transferrin) in each sample. The changes in the protein concentrations were statistically analyzed. On day-4, the relative intensity of the ~200 KDa serum protein band level decreased to 79.7% (p<0.001) of its O-day level and reduced further to 63.7% (p<0.001), on day-7. After 4 days of recovery from REM sleep loss, the relative band intensity of the band increased than that of the REM sleep deprivation level and it was 83.0% (p<0.005) of its 0-day level. In contrast, in the control LPC group, the relative band intensity of the ~200 KDa band was 94% on day-4 (p<0.1) and 98% on day-7 of their 0-day level (i.e. the changes in the protein levels in LPC control rats were non-significant).

Figure 4A:
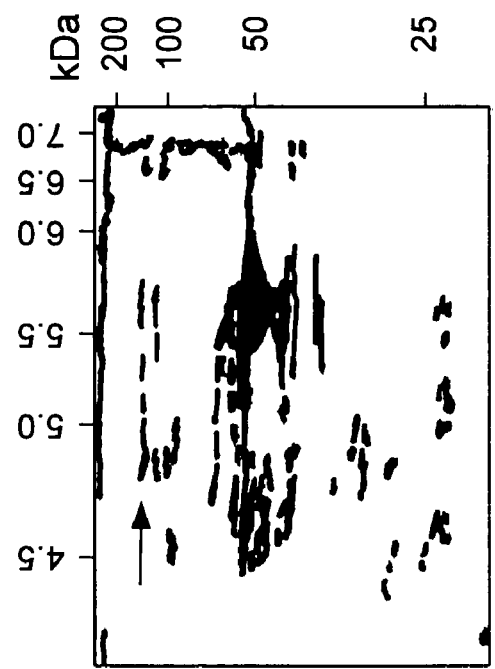
FIGS. 4A, 4B, 4C and 4D illustrate the two-dimensional SDS-PAGE protein profile of serum samples obtained at different times from one rat before REM sleep deprivation, after 4 and 7 days of REM sleep deprivation and after recovery from the effect of REM sleep deprivation.
Figure 4B:
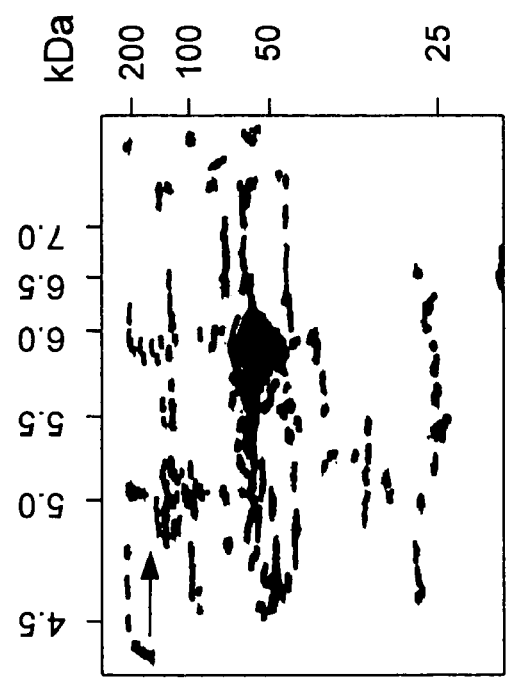
Figure 4D:
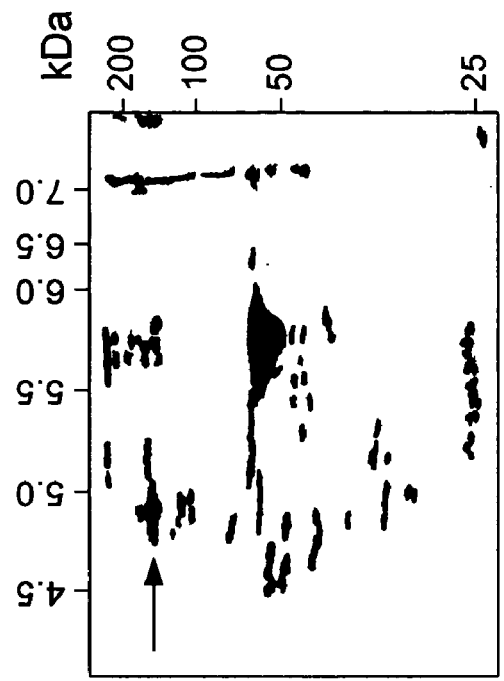
Figure 4C:
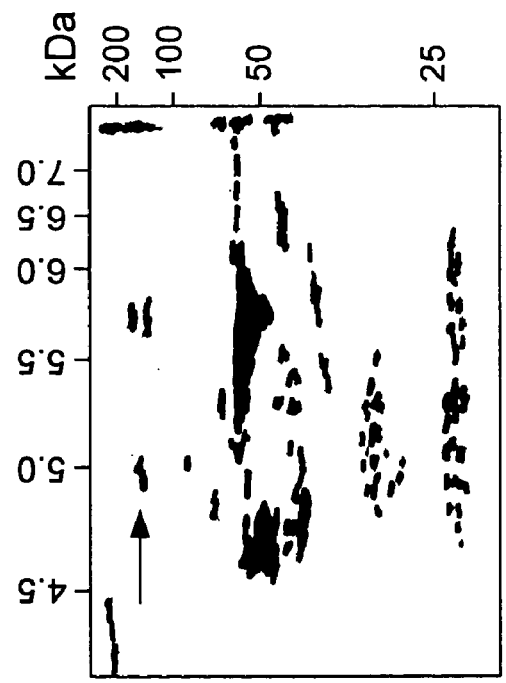

The two-dimensional SDS-PAGE protein profile of serum samples obtained at different times from one rat before REM sleep deprivation, after 4 and 7 days of REM sleep deprivation and after recovery from the effect of REM sleep deprivation are illustrated in FIGS. 4A, 4B, 4C and 4D. Comparison of the protein band intensity on different days revealed that band intensity of the ~200 KDa protein with pI between 4.5 to 5.0, was decreased after 4 days of deprivation (REMSD-4D) (FIG. 4B) as compared to its concentration in the pre-REM sleep deprivation sample (REMSD-0D) (FIG. 4A). The ~200 KDa band intensity was further decreased after 7 days of REM sleep deprivation (REMSD-7D) (FIG. 4C). However, after 4 days of recovery from REM sleep deprivation (REMSD-4R) (FIG. 4D), the band intensity of the protein increased significantly and tended to approach the pre-REM sleep deprivation level (REMSD-0D).

Figure 5B:
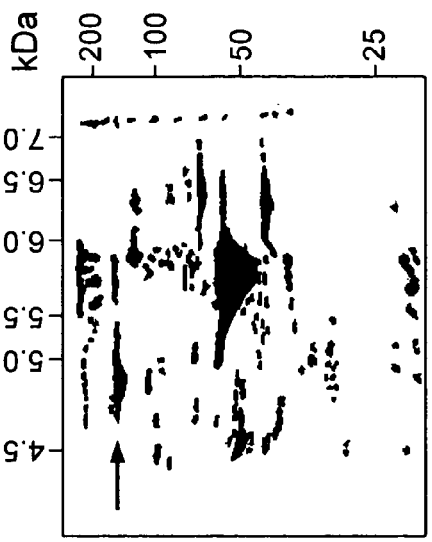
FIGS. 5A, 5B and 5C illustrate the two-dimensional SDS PAGE protein profile of serum samples obtained at the start and after maintaining the rats on large platform (LPC) which provided them with adequate opportunity to sleep including REM sleep.
Figure 5C:
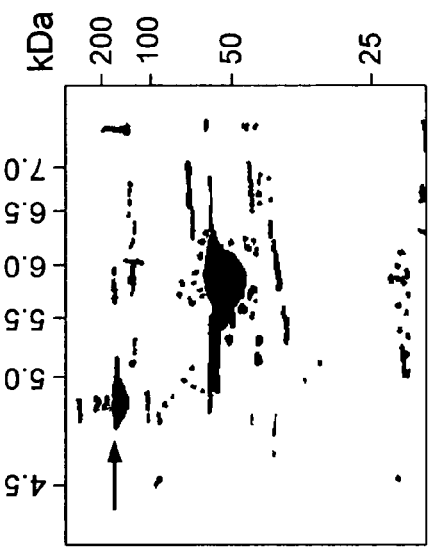
Figure 5A:
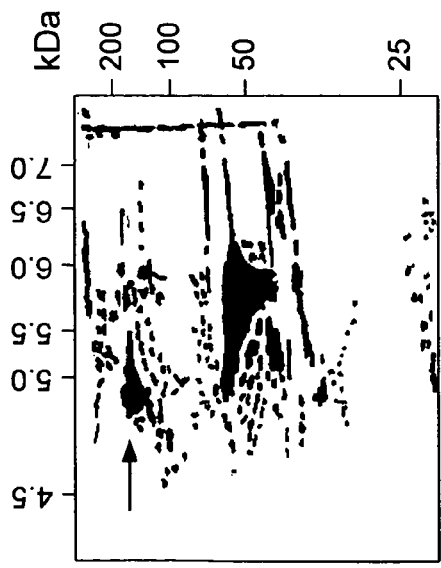

FIGS. 5A, 5B and 5C illustrates the two-dimensional SDS PAGE protein profile of serum samples obtained at the start and after maintaining the rats on large platform (LPC). Comparison of the intensity of the protein band on different days revealed that band intensity of the ~200 KDa protein with pI between 4.5 to 5.0 was not affected in serum samples obtained from LPC rats.

Figure 6A:
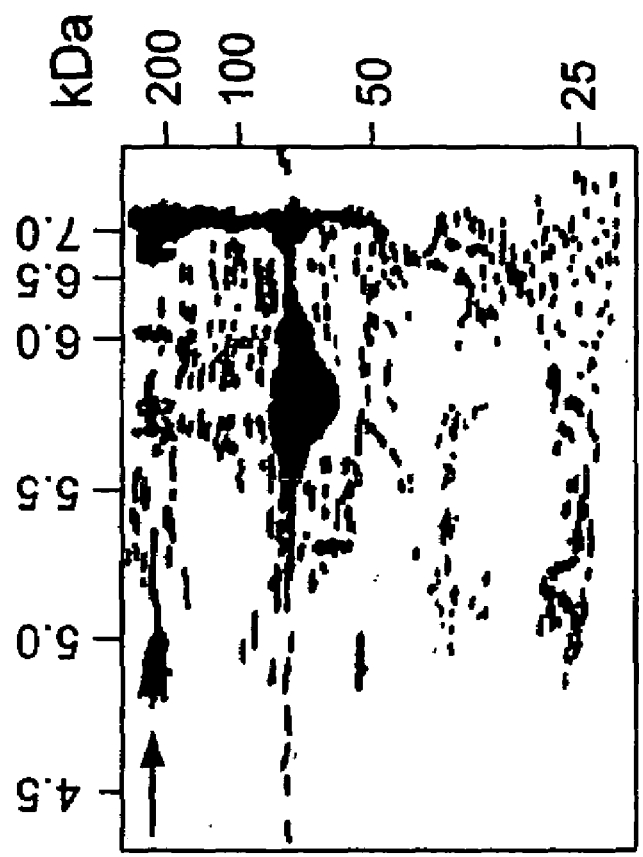
FIGS. 6A and 6B illustrate the two-dimensional SDS PAGE protein profile of serum samples of one rat obtained before (SC-O Hr) and after the rat was put for vigorous swimming (made to swim for 6 Hr (SC-6 Hr) as control).
Figure 6B:
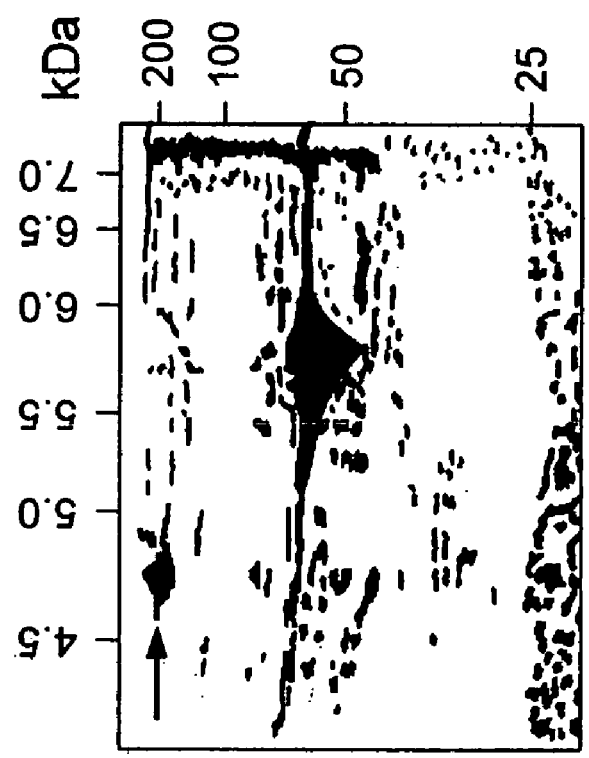

The two-dimensional SDS PAGE protein profile of serum samples obtained before (SC-0 Hr) and after a rat was made to swim for 6 Hr (SC-6 Hr) as control is illustrated in FIGS. 6A and 6B. Comparison of the ~200 KDa band intensity in SC-6 Hr sample with its own level in SC-0 Hr, revealed that unlike the REM sleep deprived rat, the protein level remained unchanged after swimming. This ruled out any possible effect of heightened muscle activity that is associated with REM sleep deprivation in flowerpot method as a cause of reduction of serum ~200 KDa protein level after REM sleep deprivation. This further proved that reduction of the ~200 KDa protein level in rat serum is likely to be a function of REM sleep loss in the rat.

Figure 7:
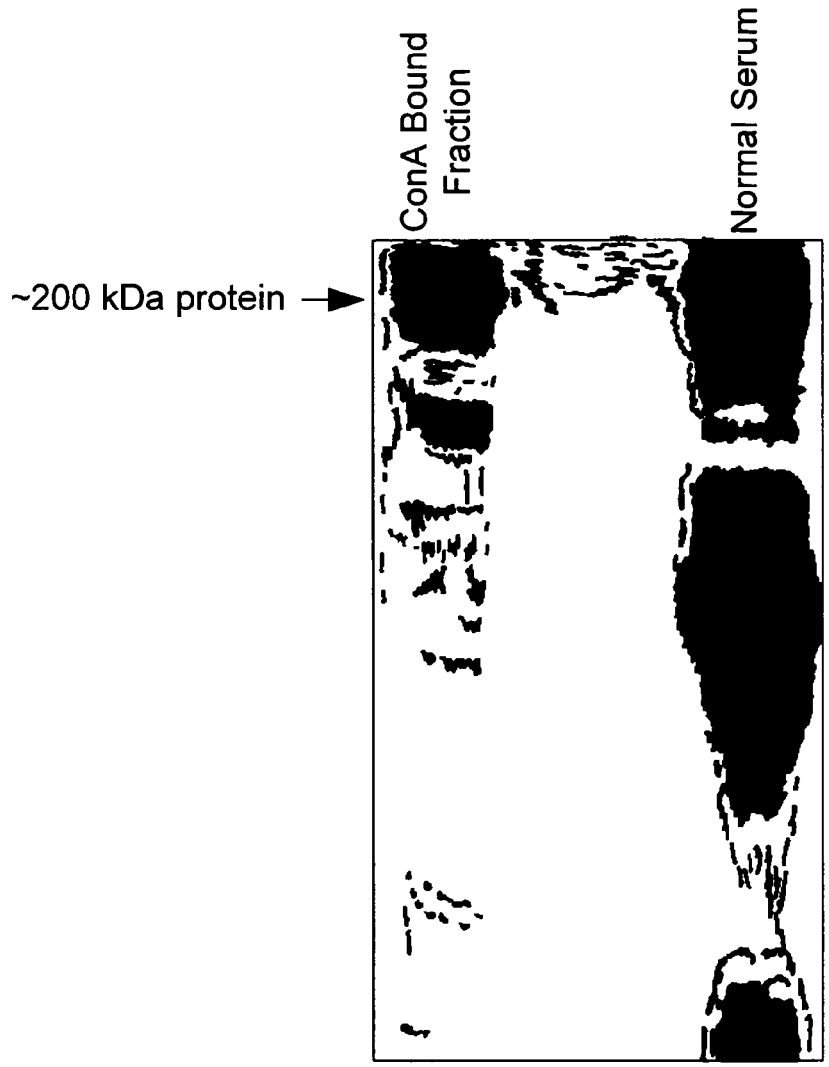
FIG. 7 shows that since the protein was bound to Concanavalin A (Con A) during fractionation, it is a glycosylated protein.

From FIG. 7, it can be seen that since the protein was bound to Concanavalin A (Con A) during fractionation, it is a glycosylated protein.

ConA is a lectin having high affinity to bind manose and glucose groups. However, the conA bound proteins can be eluted through its highest affinity binding to alpha-methyl D mannoside, thereby releasing the other bound proteins usually with lower affinities.

Materials: Sample:
Partially purified rat serum protein fraction containing our protein.

Reagents and Recipes:
5 ml of Con A sepharose
100 mg of DEAE matrix bound fraction of serum proteins
α-methyl-D-mannoside (1M) in Con A buffer
Con A buffer:
0.15 M NaCl
1 mM CaCl2
1 mM MnCl2
0.01M PBS pH 7.4

Method:
One ml of Con A sepharose was taken in a few tubes and washed with Con A buffer three times. One hundred micro grams of total proteins in 500 ul of Con A binding buffer was added to Con A sepharose taken in a glass tube. The tube was incubated overnight at 4° C. with continuous shaking.

1. The supernatant was discarded and the matrix was washed with Con A buffer 5 minutes each for eight times.
2. Five hundred microliter of a-methyl D mannoside (1M) was added to the matrix and the mixture was incubated for one hour at 4° C.
3. The matrix bound proteins were eluted in the supernatant. The eluent was analyzed in SDS PAGE.

Figure 8:
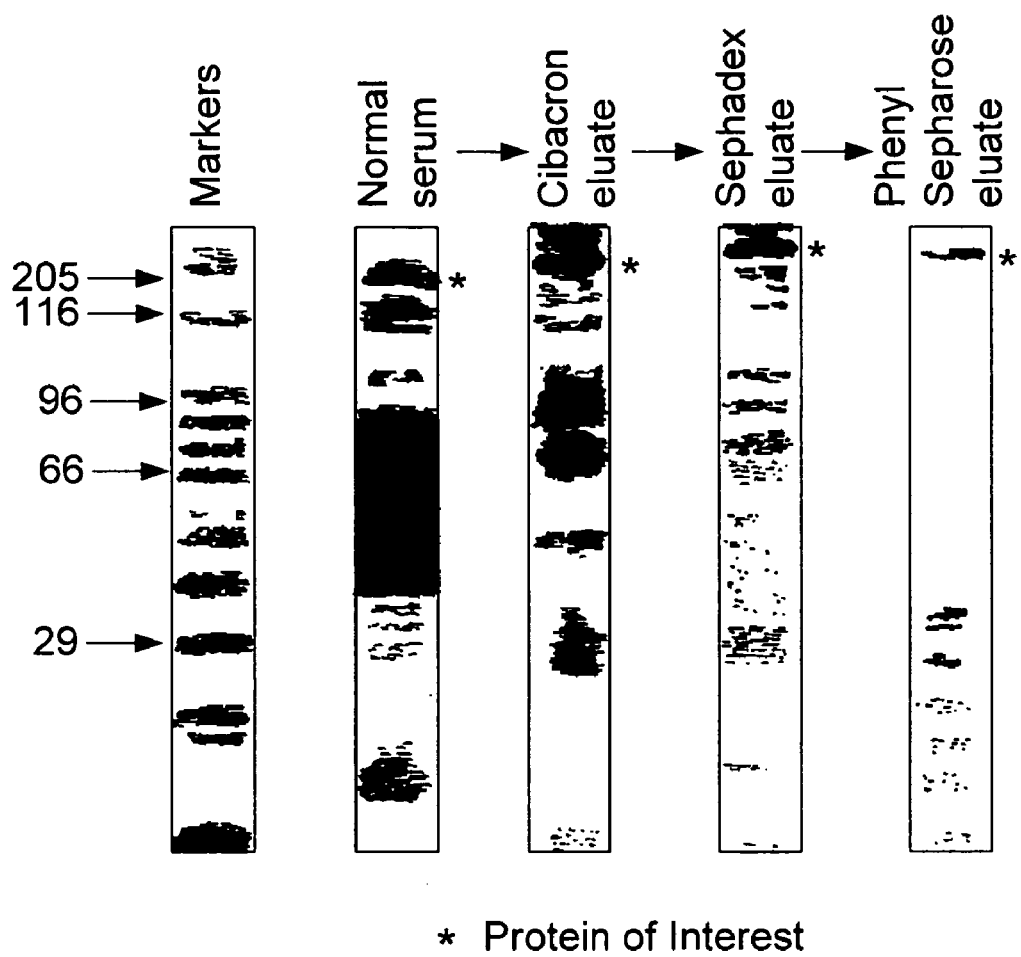
FIG. 8 shows the purified protein.

It can be seen from FIG. 8 that the protein was purified. A single band of the protein can be seen in the last lane.

Sequencing of the 200 kDa Protein (Commercially Done):
The ~200 KDa protein band from two-dimensional GEL was excised and subjected to Edman degradation using cLC Procise sequencer. The partial N-terminal 11 AA sequence of the protein could be determined at I picomole level. In several cycles more than one PTH-aminoacid could be identified. Therefore, the sequence homology search was performed using PROWL.

Also, the ~200 KDa protein band excised from 2-Dimensional SDS PAGE was in-gel digested with trypsin and 18 peptide fraction was obtained. The extracted fragments were desalted and their mass map generated by MALDI-TOF MS. The mass map was searched against All-taxa as well as rattus NCBlnr proteome database using the ProFound algorhithm. Mass map of 11 out of the 18 peptide matched and the protein was finally positively identified as Alpha-I proteinase inhibitor-III variant 1. The sequence of the protein is shown in FIG. 9.

Figure 10:
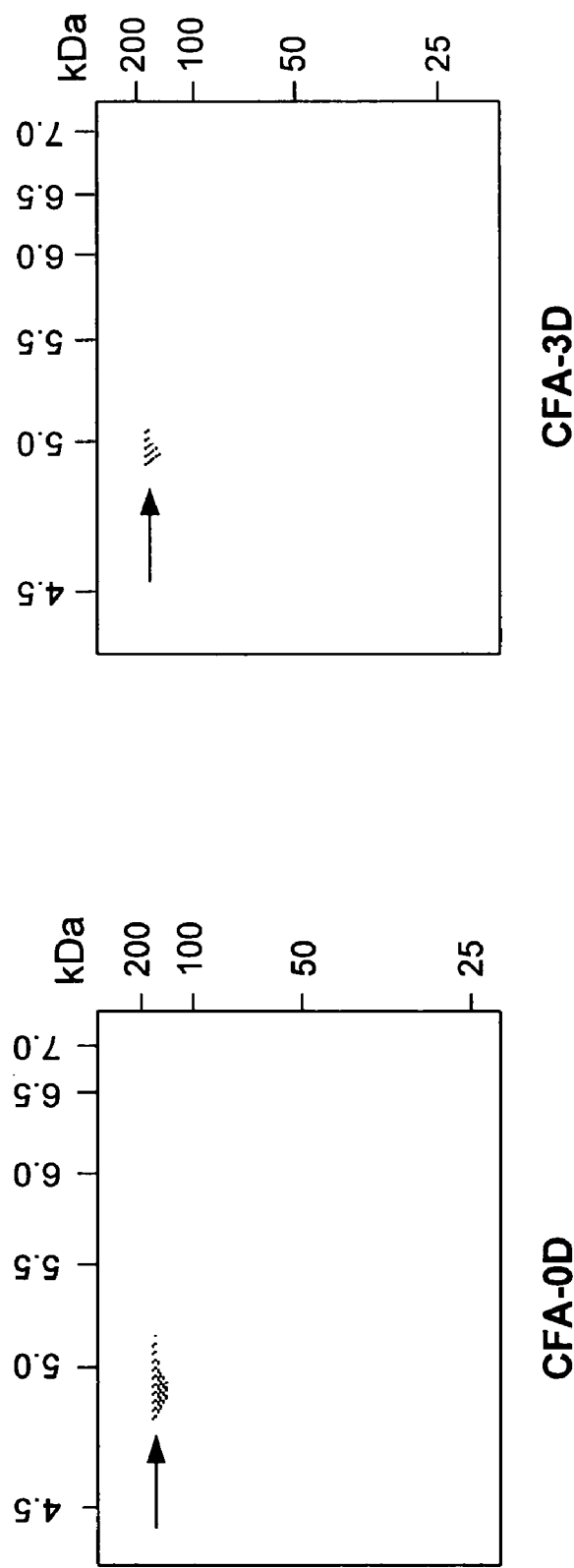
FIG. 10 shows Western Blot in two-dimensional GEL that the ~200 KDa protein was reduced in the serum if the rats were injected with CFA (complete Freund's adjuvant), that is known to cause acute phase response.

From FIG. 10, it can be seen that since the protein, Alpha-I proteinase inhibitor-III variant I, is one of the very few negative acute phase response proteins, it was tested if it was regulated by treatment to rats that caused an acute phase response. This figure shows Western Blot in two-dimensional GEL that the ~200 KDa protein (our protein) was reduced in the serum if the rats were injected with CFA (complete Freud's adjuvant), that is known to cause acute phase response. CFA (250 uL i.p.) was injected twice at a gap of 12 hrs. Since the antibody picked up the protein, it may be said with certainty that the protein was the same protein that reduced after REM sleep deprivation.

Figure 11:
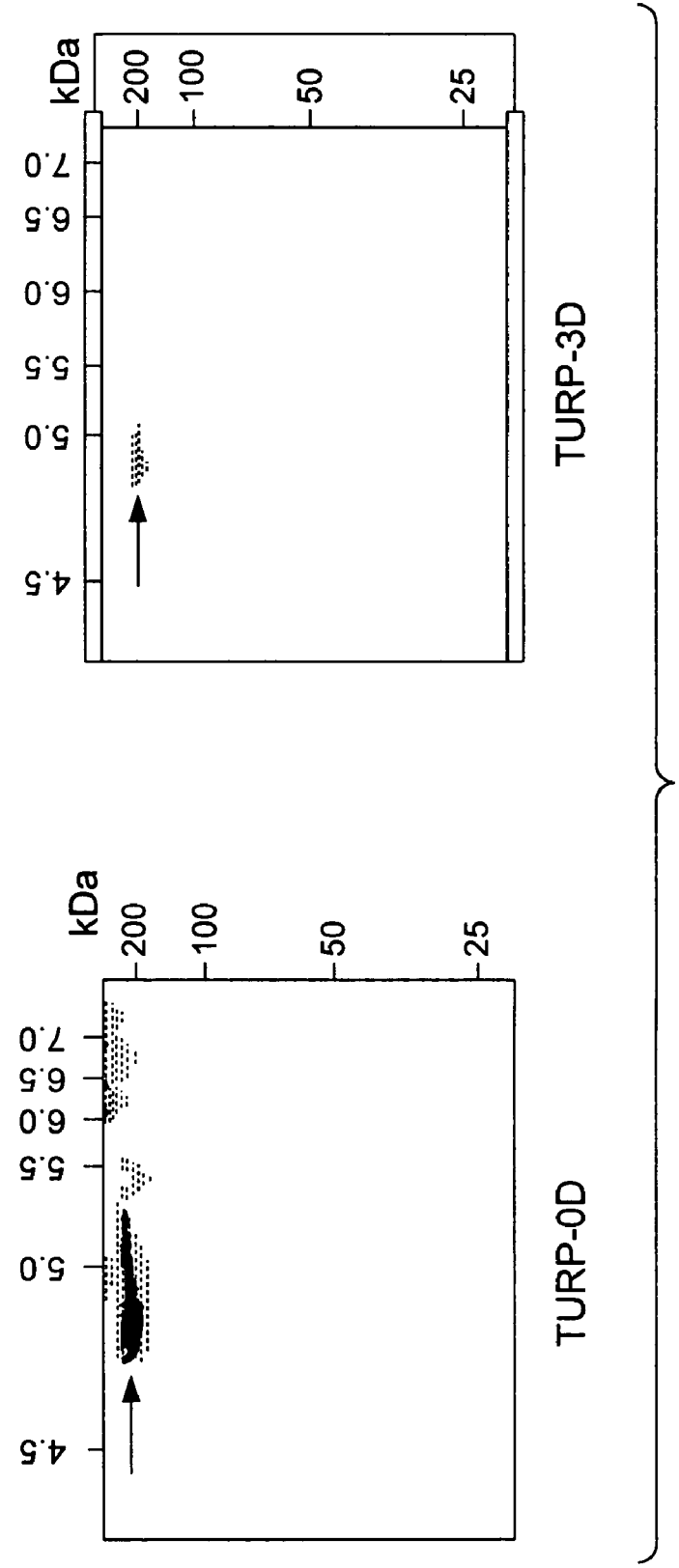
FIG. 11 shows the same as FIG. 10, but the protein profile was after injecting the rats with turpentine oil (single close 0.5 ml subcutaneous) that is known to induce acute phase response.

FIG. 11 is same as FIG. 9, but the protein profile was after injecting the rats with turpentine oil (single close 0.5 ml subcutaneous) that is known to induce acute phase response. This figure shows Western Blot in two-dimensional GEL that the ~200 KDa protein (our protein) was reduced in the serum if the rats was injected with turpentine oil that is known to cause acute phase response.

Similarly, results of injecting rats with interleukin 6 (IL6) can be seen from FIG. 12. Interleukin 6 (IL6) was injected (2500 IU i.p.) twice at an interval of 12 hrs and the effect on our protein was immuno-tested (2 dimensional—Western Blot). It has been reported that in the literature that in several diseased conditions viz. rheumatoid arthritis, fever, ageing, etc. where REM sleep is reduced, IL6 is increased. Hence, we injected IL6 in rats and estimated the concentration of our protein of interest. It was found that IL6 also reduced our protein of interest as shown in this figure.

The invention claimed is:

1. A method of diagnosing and/or identifying REM sleep loss in a mammal which comprises obtaining a blood sample of the mammal, isolating the serum from the blood sample, allowing the mammal to undergo adequate sleep, obtaining a second blood sample from said mammal, isolating the serum from said second blood sample, subjecting said first and second serum samples to electrophoresis, comparing the results of said electrophoresis of said first and second serum samples, a reduction of ~200 kDa protein band in the first serum sample as compared to the second serum sample indicating REM sleep deprivation in said mammal.

2. A method as claimed in claim 1 wherein said protein is glycosylated protein.

3. A method as claimed in claim 2 wherein said glycosylated protein is Alpha-1 proteinase inhibitor-III variant I.

4. A method as claimed in claim 1 wherein said protein has the sequence shown in SEQ ID NO: 1.

5. A method as claimed in claim 1 wherein said mammal is a rat.

6. A method as claimed in claim 1 wherein said mammal is a human.

* * * * *